United States Patent
Edmonson et al.

(10) Patent No.: US 8,420,382 B2
(45) Date of Patent: *Apr. 16, 2013

(54) ACOUSTIC WAVE BIOSENSOR FOR THE DETECTION AND IDENTIFICATION OF CHARACTERISTIC SIGNALING MOLECULES IN A BIOLOGICAL MEDIUM

(75) Inventors: Peter J. Edmonson, Hamilton (CA); William D. Hunt, Decatur, GA (US); Desmond D. Stubbs, Riverdale, GA (US)

(73) Assignee: P.J. Edmonson Ltd. (CA)

( * ) Notice: Subject to any disclaimer, the term of this patent is extended or adjusted under 35 U.S.C. 154(b) by 480 days.

This patent is subject to a terminal disclaimer.

(21) Appl. No.: 12/636,252

(22) Filed: Dec. 11, 2009

(65) Prior Publication Data

US 2010/0178688 A1    Jul. 15, 2010

Related U.S. Application Data

(63) Continuation of application No. 11/226,261, filed on Sep. 15, 2005, now Pat. No. 7,651,843.

(60) Provisional application No. 60/613,262, filed on Sep. 27, 2004.

(51) Int. Cl.
  *C12M 1/34* (2006.01)
(52) U.S. Cl.
  USPC ........................ 435/287.1; 435/7.2; 257/254
(58) Field of Classification Search ............... 435/287.1, 435/7.2; 257/254
  See application file for complete search history.

(56) References Cited

U.S. PATENT DOCUMENTS

| | | | | |
|---|---|---|---|---|
| 5,436,147 A | * | 7/1995 | Pegg et al. | 435/181 |
| 6,846,654 B1 | * | 1/2005 | Blackburn et al. | 435/7.1 |
| 2005/0082175 A1 | * | 4/2005 | Saini et al. | 205/777.5 |

OTHER PUBLICATIONS

S.A. Voloshin, A.S. Kaprelyants, "Cell-Cell Interactions in Bacterial Populations", Jul. 9, 2004, Biochemistry (Moscow), vol. 69, No. 11, 2004, pp. 1268-1275.*
Dicke et al.; "Infochemical Terminology; Based on Cost-Benefit Analysis Rather than Origin of Compounds?"; Functional Ecology 2.2 (1988); p. 131-139.
Jones et al.; Inhibition of *Bacillus anthracis* Growth and Virulence-Gene Expression by Inhibitors of Quorum-Sensing.; The Journal of Infectious Diseases 191 (2005); p. 1881-1888.
Sbarbati et al.; "Allelochemical Communication in Vertebrates: Kairomones, Allomones and Synomones."; Cells Tissues Organs 183 (2006); p. 206-219.

(Continued)

*Primary Examiner* — William H Beisner
*Assistant Examiner* — Danielle Henkel
(74) *Attorney, Agent, or Firm* — Steven M. Greenberg; Carey Rodriguez Greenberg O'Keefe, LLP

(57) ABSTRACT

An acoustic wave biosensor comprises a plurality of spaced apart electrodes disposed on a substrate of piezoelectric material and having a biolayer matched to a specific type of autoinducer signaling molecule to be detected. The biolayer comprises a layer of heterobifunctional molecules disposed on the electrodes and on the piezoelectric material between the electrodes, and a plurality of bioreceptor molecules which bind exclusively with the specific type of autoinducer signaling molecule to be detected. The bioreceptor molecules are supported by the layer of heterobifunctional molecules, and a hydrogel layer surrounds the bioreceptor molecules to support a three-dimensional structure thereof. The bioreceptor molecules can bind with the specific type of autoinducer signaling molecule to be detected, and the biolayer is reactive thereto such that corresponding autoinducer signaling molecules bind to the biolayer and detectably vary acoustic characteristics of the acoustic wave biosensor.

1 Claim, 6 Drawing Sheets

OTHER PUBLICATIONS

Fox; "Non-Traditional Targets of Endocrine Disrupting Chemicals: The Roots of Hormone Signaling."; Integrative and Comparative Biology 45 (2005); p. 179-188.

Ndagijimana, et al.; "Two 2[5H]-Furanones as Possible Signaling Molecules in *Lactobacillus helveticus*."; Applied and Environmental Microbiology vol. 72 No. 9 (2006); p. 6053-6061.

Beale et al.; "*Caenorhabditis elegans* Senses Bacterial Autoinducers."; Applied and Environmental Microbiology; vol. 72 No. 7 (2006); p. 5135-5137.

Lucklum et al.; "Roll of Mass Accumulation and Viscoelastic Film Properties for the Response of Acoustic-Wave-Based Chemical Sensors." Analytical Chemistry 71:13 (1999); p. 2488-2496.

Marxer et al.; "Study of adsorption and viscoelastic properties of proteins with a quartz crystal microbalance by measuring the oscillation amplitude."; Journal of Colloid and Interface Science 261 (2003); p. 291-298.

\* cited by examiner

ACOUSTIC WAVE BIOSENSOR FOR THE DETECTION AND IDENTIFICATION OF CHARACTERISTIC SIGNALING MOLECULES IN A BIOLOGICAL MEDIUM

CROSS-REFERENCE TO RELATED APPLICATIONS

This application is a continuation of U.S. patent application Ser. No. 11/226,261 filed on Sep. 15, 2005, which claims priority from U.S. Provisional Patent Application No. 60/613,262 filed Sep. 27, 2004, the teachings of each of which are hereby incorporated by reference in their entirety.

FIELD OF INVENTION

This invention relates to the detection of signaling molecules in a biological environment.

BACKGROUND OF INVENTION

Certain living species release and detect natural chemicals which act as signaling methods to other like neighbors. Cell to cell communication (quorum-sensing) within bacterial populations can direct certain internal processes, such as cell division, sporulation, genetic transformation and virulence. Similar signaling molecules, such as plant hormones, also control the way plants grow and develop. Bacteria, plant species and other micro-organisms release small signaling molecules into their intercellular space to communicate both with their inter-specific and intraspecific neighbors. Certain bacteria and micro-organisms grouped in critical populations exhibit more information via the signaling molecules than the individual bacterium or micro-organism.

Traditional testing methods for bacteria are relatively expensive and time consuming. Most common testing methods require an environmental or product sample which is incubated in a separate media until enough bacteria exist to visually confirm their presence via culture plates or more elaborate immunoassays. These known methods are not real-time bacteria detection schemes. Other known detection methods, such as polymerase chain reaction (PCR), are faster but require a more complicated and expensive procedure. Many known bioassay sensors are not robust enough and therefore not suited for portable applications, because they require specific growing media to operate. Known biosensors also have difficulty adequately stating a limit of detection or dynamic range. The time to prediction of bacteria also depends on the response time of the bacteria cell growth.

Bacteria are single celled organisms typically 0.5 to 1 micron (µm) in diameter to 3-15 µm long (C. A. Hart, "Microterrors" Firefly Books Ltd, 2004) and are less mobile in their intercellular space than their small signaling molecules categorized as autoinducers. Acoustic wave devices have been developed for the direct detection of large bacterium, as described by Sang-Hun Lee, Desmond D. Stubbs, John Cairney, and William D. Hunt in "Rapid Detection of Bacterial Spores Using a Quartz Crystal Microbalance (QCM) Immunoassay" IEEE SENSORS JOURNAL, VOL. 5, NO. 4, AUGUST 2005. Lee et al., describe a method of instant identification of Bacillus subtilis (nonpathogenic simulant for *Bacillus anthracis*) bacterium by constructing a dual quartz crystal microbalance (QCM) immunosensing system. A set of 10-MHz AT-cut QCMs operating in thickness shear mode are employed in an enclosed flowcell. However, this method only detects the presence of a micro-organism, not the purpose of the micro-organism, such as cell division, sporulation, genetic transformation, virulence and species development.

SUMMARY OF INVENTION

In one aspect, the present invention is directed to an acoustic wave biosensor for detecting and identifying bacteria, micro-organisms or plants in a liquid or gaseous medium. The bacteria, micro-organisms or plants to be identified are of the kind which produce autoinducer signaling molecules in intercellular space.

Signaling molecules, characterized as autoinducers, diffuse more readily within the surrounding environment compared to the actual bacterium. The present invention is well suited for SAW (surface acoustic wave) geometries which are typically in the sub-micron range and can also function as RFID sensors which can be interrogated by a wireless system. SAW detectors can be small, simple in nature and provide microbial differentiation detection results quickly.

The acoustic wave biosensor comprises a plurality of spaced apart electrodes disposed on a substrate of piezoelectric material and having a biolayer matched to a specific type of autoinducer signaling molecule to be detected. The biolayer comprises a layer of heterobifunctional molecules disposed on the electrodes and on the piezoelectric material between the electrodes, and a plurality of bioreceptor molecules which bind exclusively with the specific type of autoinducer signaling molecule to be detected. The bioreceptor molecules are supported by the layer of heterobifunctional molecules, and a hydrogel layer surrounds the bioreceptor molecules to support a three-dimensional structure thereof. As a result, the bioreceptor molecules can bind with the specific type of autoinducer signaling molecule to be detected, and the biolayer is reactive to the specific type of autoinducer signaling molecule to be detected such that corresponding autoinducer signaling molecules bind to the biolayer and detectably vary acoustic characteristics of the acoustic wave biosensor.

Thus, the present invention provides acoustic wave based sensors coated with specific bioreceptor molecules which can detect small signaling molecules from an originating species and quantify the acoustic wave sensor data due to the linear relationship between the mass of the signaling molecule and the velocity of the acoustic wave and therefore identify both the presence and the purpose of the originating species.

Such biosensors can provide a medium for detecting harmful biological agents without coming into direct contact with the bacteria themselves. In addition, acoustic wave biosensor techniques permit quantification through the direct relationship between the concentrations of small signaling molecules in intercellular space to the relative amount of signaling source present. This technology can be used for the detection of *Bacillus* related species, such as *anthracis, subtilis, cereus, globigii* and other species, such as *Streptococcus pneumoniae, Staphylococcus aureus* and *Enteroccocus faecalis*. This technology can also be further used to detect sources of signaling chemicals, such as ethylene which communicates and promotes the premature ripening of foodstuffs within the agricultural industry.

The present invention is well suited for monitoring certain environments which require the detection of various species of bacteria, including but not limited to airborne microorganisms, such as *Bacillus subtilis, B. cereus, B. anthracis* and plant hormones such as ethylene. This invention can also be used for the detection of fungii microbes, including mold forming organisms, and for the detection of both vegetative and spore forms of microbes. Also, the agricultural industry can benefit from such monitoring of signaling molecules. The present invention can detect the release of certain gaseous plant hormones, such as ethylene, which affect the way plants grow and develop. Ethylene is a gaseous plant hormone which plays an important role in plant growth and development. Both fruit and flowers may ripen or blossom prematurely when exposed to ethylene. Ethylene is perceived by the agricultural industry as detrimental to product quality, and significant efforts are made to minimize its effects. The present invention also permits the detection and identification of signaling molecules of certain pests and weeds to enable the application of pesticides and herbicides to be controlled.

Advances in industrial microbiology are also major factors for innovation and progress in the food industry. Products such as yogurt, cheese, chocolate, butter, pickles, sauerkraut, soy sauce, food supplements (vitamins and amino acids), food thickeners (produced from microbial polysaccharides), alcohol (beer, whiskeys, wines) and silage for animals are all products of microbial activity. The maintenance of the fermentation process which is commonly used in industry becomes a high priority as the necessity for monitoring species population, growth and contamination becomes more stringently controlled. The present invention is thus useful in this field also.

The present invention is also useful in the counterterrorism field, particularly in respect of bioterrorism. Counter-bioterrorism applications of the invention include detecting harmful biological agents on the battle ground, in public places, including individual packages or enclosures, or in heating ventilation and air conditioning (HVAC) systems of buildings.

The present invention also has usefulness in the clinical detection of bacteria in various media, including blood and exhaled breath. For example, Bacteremia is an infection caused by the presence of bacteria in the blood. Such infection can cause damage of the heart valves, the lining of the heart and the lining of blood vessels. Early detection of elevated bacteria population in blood may mediate these symptoms. Certain pathogenic bacteria contain luxS proteins which produce the autoinducer-2 (AI-2) signaling chemicals. Such signaling chemicals assist in the co-ordinated gene expression depending upon the population density of the bacteria.

Another clinical example is the Neisseria meningitidis bacteria, which colonizes within the human nasopharynx and is the cause of meningitis. K. Winzer et al, show evidence in "sole of *Neisseria meningitidid* luxS in Cell-to-Cell Signaling and Bacteremic Infection," Infection and Immunity, Vol. 70, No. 4, pp. 2245-2248 April 2002, that *N. meningitidis* possesses a functional luxS protein which is necessary for AI-2 production and full meningoccal virulence. Further detection of signaling molecules within the nasopharynx can lead to the detection of the *Neisseria meningitides* bacteria. Technology incorporating the present invention can also be utilized in hospitals, schools, office buildings, transportation centers and any other environments to aid in determining signaling chemical concentrations. Signaling molecule detection systems can be implemented with a small portable device or with fixed devices. In addition, the present invention can be used for the determination of signaling chemicals in restaurants and other food handling facilities to monitor the amount of bacterial organisms around work stations.

This invention could also be used as a feedback element within a control system for the detection and remediation of certain biological entities. Such a control system would identify a biological entity and then apply appropriate corrective measures, such as pesticides, herbicides or other autoinducer degrading enzymes which would minimize the biological entity. For example, in the technique described by Jones et al "Inhibition of *Bacillus anthracis* Growth and Virulence-Gene Expression by Inhibitors of Quorum-Sensing," Journal of Infectious Diseases, June 2005, the use of antibiotics could be replaced by the detection and use of signaling molecule inhibitors in accordance with the present invention.

An analogy of this invention would be a microphone (biosensor) placed outside an open door of a room containing an unknown amount of people (bacteria or plants) from various different countries (various inter- and intraspecies). The microphone does not come into contact with the people but rather listens to the chatter (autoinducers or biological hormones) generated by the people. Using an algorithm attached to the microphone, it is then possible to calculate the estimated number of different dialects from various countries that the people originated from, the number of people associated with each specific dialect and the purpose or intent of each conversation.

DESCRIPTION OF THE DRAWINGS

Embodiments of the invention will now be described, by way of example, with reference to the accompanying drawings, of which.

DESCRIPTION OF PREFERRED EMBODIMENTS

Bacteria are for the most part free-living and, when provided with habitable environments, they can reproduce by the process of binary fission such that one bacterial cell can produce up to 10 million descendants within 18 to 2 hours. The physical shape of bacteria may be rod shaped (bacilli), spherical (cocci), or spiral (spirochaetes). Also, bacilli can be either straight or bent, and cocci can be arranged in pairs (diplococci), in clusters (staphylococci) or in long chains (streptococci). The design of a selective detection system dependent on the physical shape of specific bacteria would be an enormous challenge. However, within the framework of quorum sensing, it has been reported by S. A. Voloshin & A. S. Kaprelyants, "REVIEW: Cell-Cell Interactions in Bacterial Populations," Biochemistry (Moscow), Vol 69, No. 11, 2004, pp. 1268-1275, that it is possible to use certain detection proteins which can selectively distinguish between the chemical characteristics of the signal molecules (autoinducers) used for cell-cell interactions in bacterial populations. Detecting such chemical signal molecules is a precursor to the whereabouts of specific bacteria.

Figure 1:
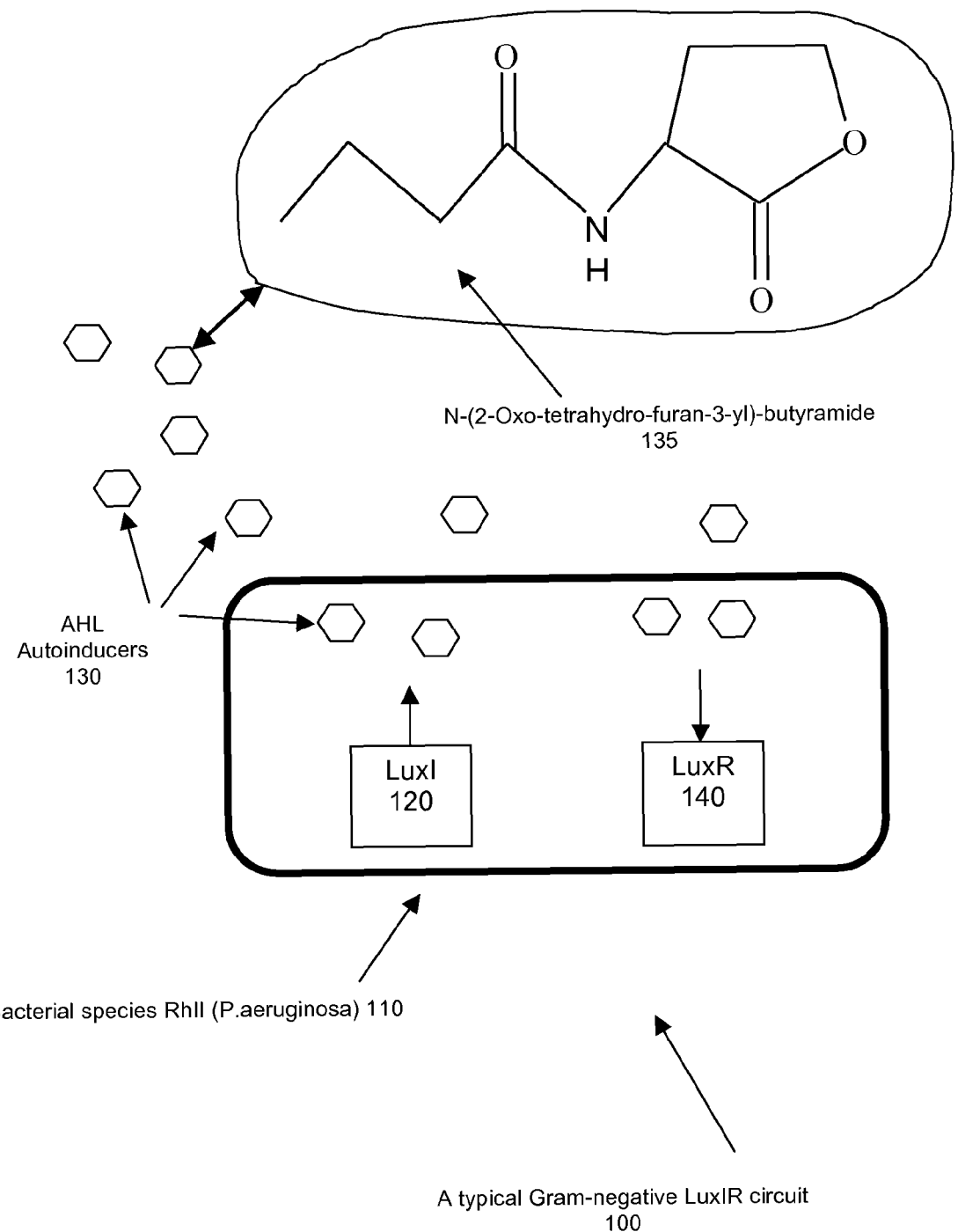
FIG. 1 is a diagrammatic view showing a gram-negative bacteria cell, species RhlI (*P. aeruginosa*), producing AHL autoinducers, namely N-(2-Oxo-tetrahydro-furan-3-yl)-butyramide.

Numerous pathogenic bacteria contain certain proteins, which are required for the production of autoinducers as outlined by Michiko Taga and Bonnie Bassler, "Proc. Nat. Acad. Sci.", vol. 100, pp. 14549-14554, November 2003. The nature of autoinducers generated by certain proteins within bacteria is dependent on whether the bacteria cell is gram-positive or gram-negative. Gram-negative cells generate low molecular weight signaling molecules such as N-acyl homoserine lactones (AHLs). Gram-positive cells secrete more complex but still relatively small oligopeptides or proteins. FIG. 1 depicts a typical Gram-negative LuxIR circuit 100 consisting of a bacteria cell, species RhII (*P. aeruginosa*) 110 producing within the LuxI proteins 120 AHL autoinducers 130 of composition N-(2-Oxo-tetrahydro-furan-3-yl)-butyramide 135. The AHL autoinducers are received by the LuxR protein 140 and affect the virulence enzyme production and bio film formation of the species RhII (*P. aeruginosa*) 110.

Figure 2:
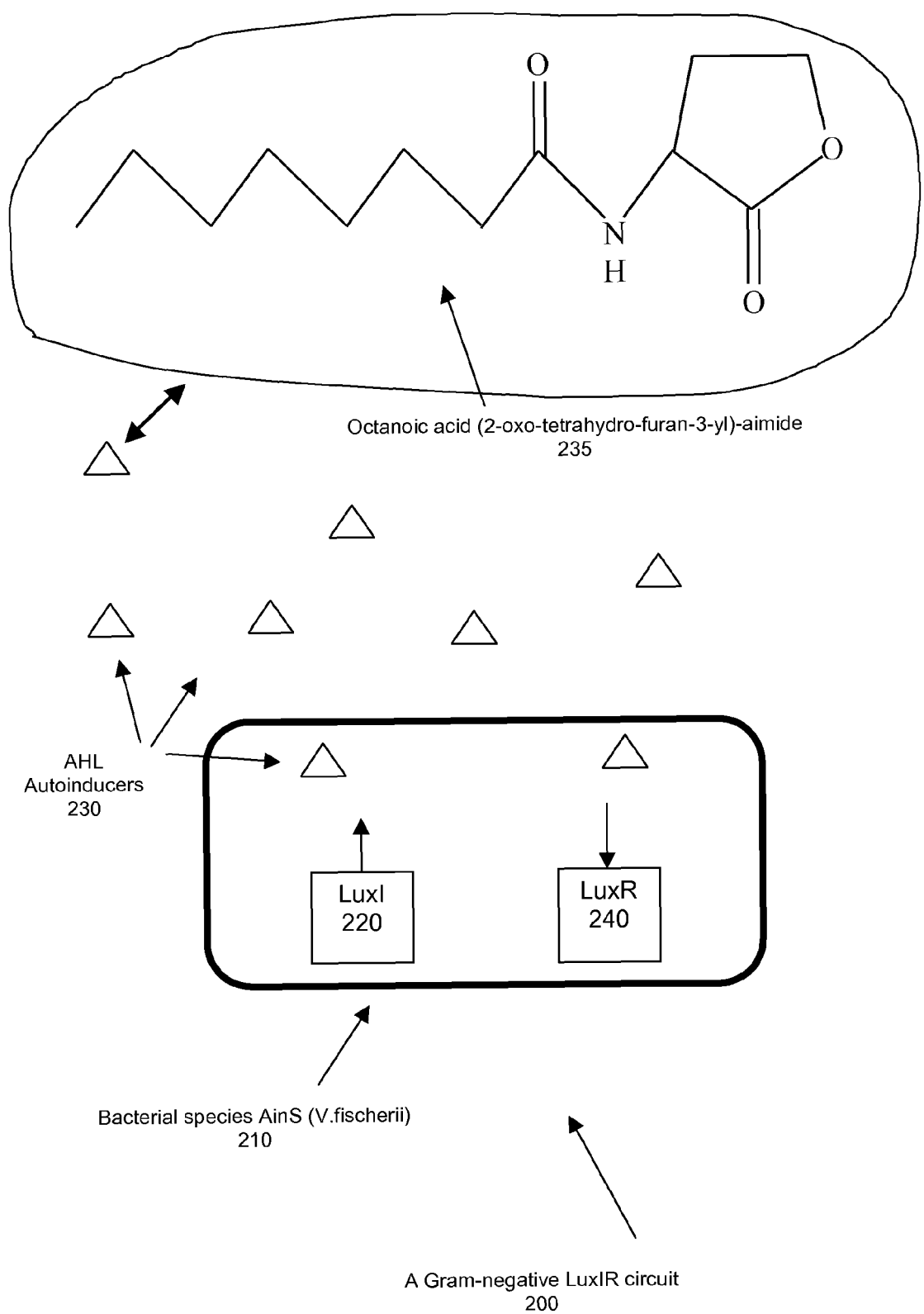
FIG. 2 is a similar view showing a gram-negative bacteria call, species AinS (*V. fischerii*), producing AHL autoinducers, namely octanoic acid (2-oxo-tetrahydro-furan-3-yl)-aimide.
Figure 3:
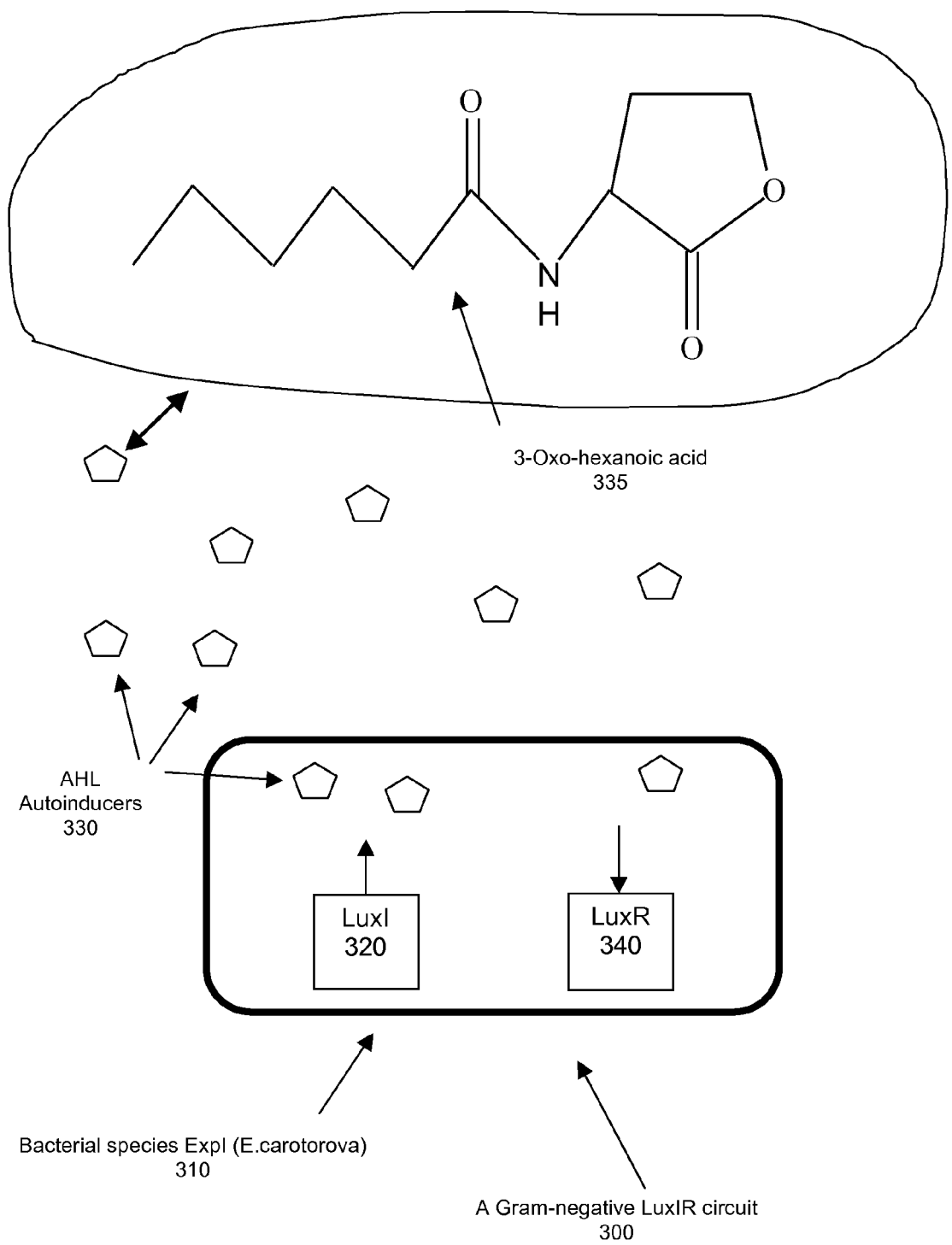
FIG. 3 is a similar view showing a gram-negative bacteria cell, species ExpI (*E. carotorova*), producing AHL autoinducers, namely 3-Oxo-hexanoic acid.
Figure 4:
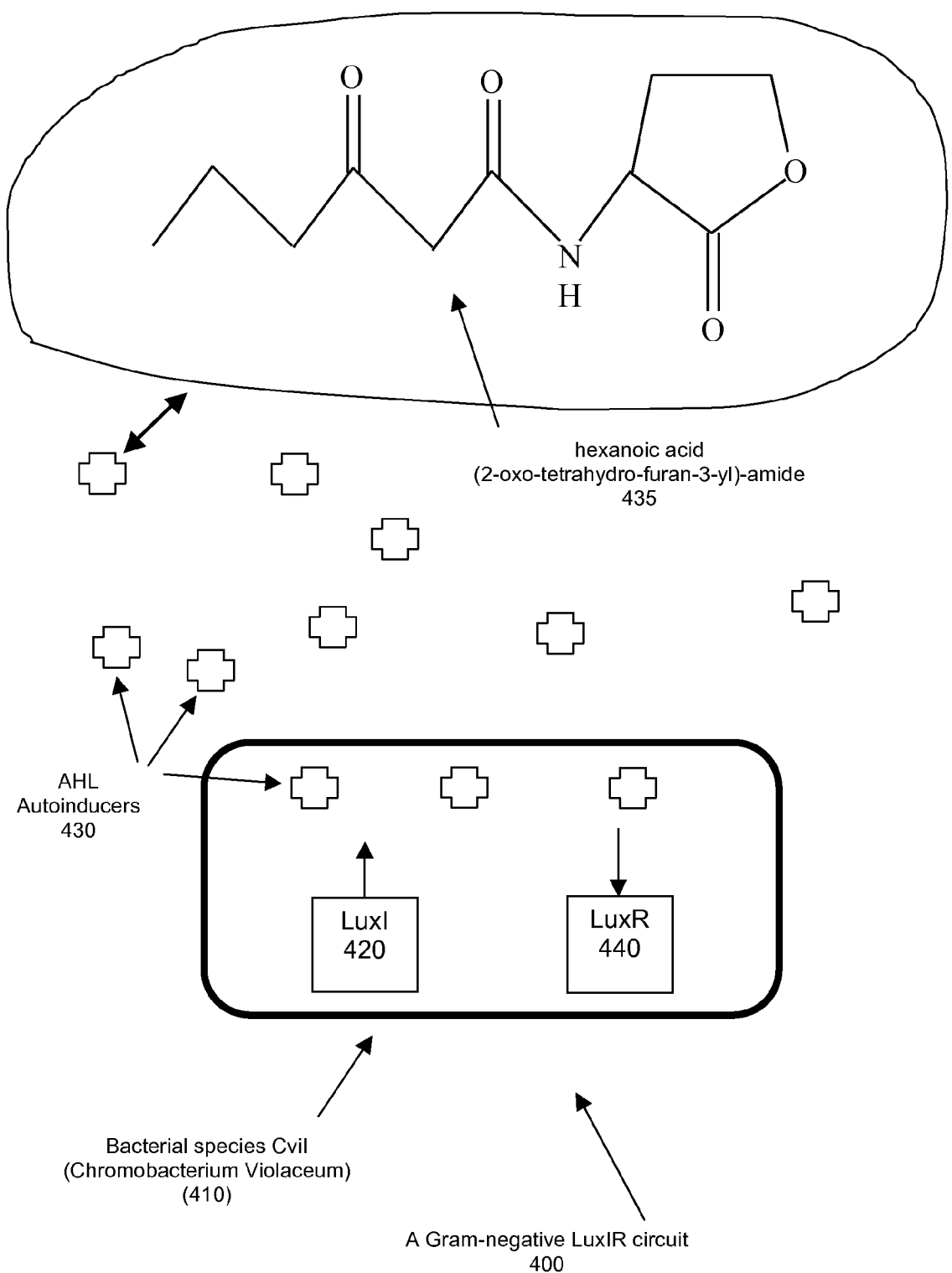
FIG. 4 is a similar view showing a gram-negative bacteria cell, species CviI (*Chromobacterium Violaceum*), producing AHL autoinducers, namely hexanoic acid (2-oxo-tetrahydro-furan-3-yl)-amide.

Analogous AHL autoinducers share a common homoserine lactone moiety and typically differ only in their acyl side chain moieties. FIG. 2 depicts another typical Gram-negative LuxIR circuit 200 consisting of a bacteria cell, species AinS (*V. fischerii*) 210, producing within the LuxI proteins 220 AHL autoinducers 230 of composition Octanoic acid (2-oxo-tetrahydro-furan-3-yl)-aimide 235. The AHL autoinducers are received by the LuxR protein 240 and affect the bioluminescence of the species AinS (*V. fischerii*) 210. FIG. 3 depicts another typical Gram-negative LuxIR circuit 300 consisting of a bacteria cell, species ExpI (*E. carotorova*) 310, producing within the LuxI proteins 320 AHL autoinducers 330 of composition 3-Oxo-hexanoic acid 335. The AHL autoinducers are received by the LuxR protein 340 and affect the synthesis of carbapenom (an antibiotic) of the species ExpI (*E. carotorova*) 310. FIG. 4 depicts another typical Gram-negative LuxIR circuit 400 consisting of a bacteria cell, species CviI (*Chromobacterium Violaceum*) 410, producing within the LuxI proteins 420 AHL autoinducers 430 of composition hexanoic acid (2-oxo-tetrahydro-furan-3-yl)-amide 435. The AHL autoinducers are received by the LuxR protein 440 and affect the generation of a deep violet pigment named violacein of the species CviI (*Chromobacterium Violaceum*) 410.

For the gram-positive bacterial species *Bacillus anthracis*, a signaling molecule autoinducer-2 (AI-2) is synthesized via a LuxS-type protein. The LuxS protein converts S-ribosylhomocysteine to 4,5-dihydroxyl-2,3-pentanedione, catalysing the formation of the AI-2.

The species RhII (*P. aeruginosa*) 110, AinS (*V. fischerii*) 210, ExpI (*E. carotorova*) 310, CviI (*Chromobacterium Violaceum*) 410 and similar other species produce a variety of signaling molecules which support diverse functions such as cell division, sporulation, genetic transformation, virulence and species development. Detection of a specific autoinducer/signalling molecule from the same micro-organism or plant depends on the specificity of the bioreceptor layer of the detection system.

Figure 5:
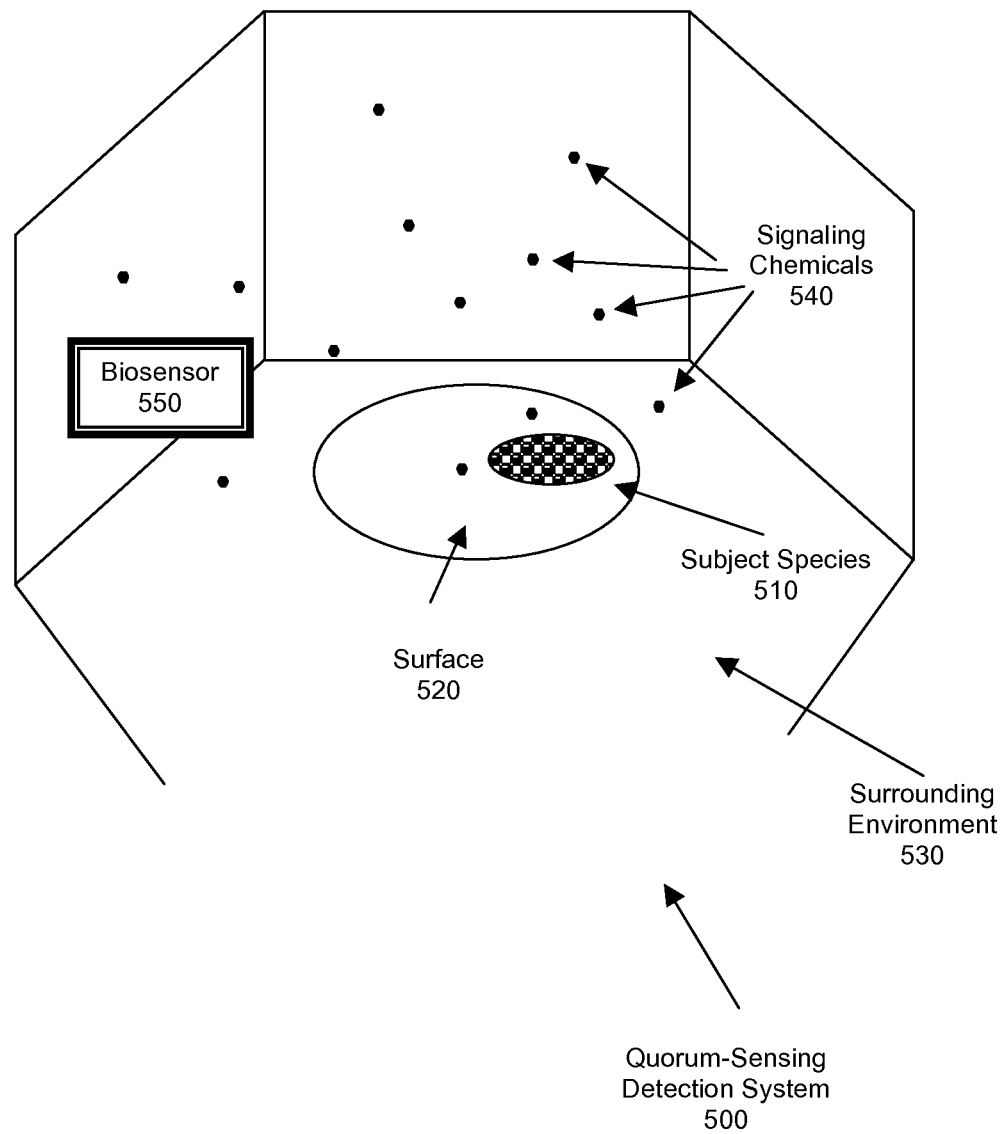
FIG. 5 is a diagrammatic view of a quorum-sensing system depicting *Bacillus anthracis* and their AHL autoinducers diffusing a few meters away.

The small signaling molecules produced by bacteria have a very low vapor pressure and can only be detected by using very sensitive sensors. An example of how quorum sensing can be used for the detection and purpose of harmful biological agents without coming into physical contact with the bacterium themselves in accordance with the invention is shown in FIG. 5. Within a quorum-sensing detection system 500, a subject species 510 which may for example contain *Bacillus anthracis* is positioned on a surface 520 within an environment 530 such as a room, office cubicle, warehouse or any military/bioterrorism scenario where harmful biological threats may be present.

Signaling chemicals 540 such as autoinducers AI-2 specific to *Bacillus anthracis* would be present in the intercellular vapor space surrounding the subject species 510 within the environment 530. An acoustic wave biosensor 550 is positioned at a safe distance from the subject species 510 to sample the surrounding vapor for the signaling chemicals 540 within the environment 530 and perform a real-time evaluation within the algorithm of the acoustic wave biosensor. The acoustic wave biosensor 550 shown in FIG. 5 may have the form factor of a self contained wireless handheld type of unit or a remote fixed monitoring station with wired or wireless capability. The acoustic wave biosensor may be an RFID type sensor as described by Edmonson et al. in "A surface acoustic wave sensor or identification device with biosensing capability", U.S. patent application Ser. No. 11/139,477 filed May 31, 2005, the contents of which are hereby incorporated herein by reference.

A further advantage of using an acoustic wave biosensor is to capitalize on the promiscuous nature of the bioreceptors so that detection of multiple analogs of signaling chemicals is possible. An example of such detection using a multiple acoustic wave detector is described in Edmonson et al. "Differentiation and identification of analogous chemical or biological substances with biosensors", U.S. patent application Ser. No. 11/088,809 filed Mar. 25, 2005, the contents of which are hereby incorporated herein by reference.

The scenario seen in FIG. 5 can be repeated for numerous other examples. In other words, other instances in which pathogenic bacteria with Gram-negative or Gram-positive cells generate autoinducers can be applied to the scenario seen in FIG. 5. For agricultural examples, the plant hormone ethylene can be detected to control premature ripening of certain fruits within warehouses. For background information in this respect, see P. J. Davies, "Plant Hormones, Biosynthesis, Signal Transduction, Action." Kluwer Academic Publishers, Dordrecht, The Netherlands, 2004. The commonality is that the acoustic wave biosensor 550 must have its biolayer matched to the quorum-sensing chemical signaling molecules, so that the specific bioreceptor molecules on the biosensor are receptive to the analogous signaling chemical. Further examples for the detection of molds and fungi can also be applied to the scenario shown in FIG. 5. It should also be noted that the intercellular space in which the autoinducers/signaling chemicals are present may be a liquid or a gaseous medium with the detection taking place within the liquid or gaseous medium.

A major advantage of detecting autoinducers within an intercellular space is that both the presence and purpose of bacteria rather than only the actual bacteria themselves can be identified. This is especially essential for harmful bacteria. Further, it permits the use of detectors based on thin-film fabrication with sub-micron geometries. Acoustic wave biosensors and other similar nanotechnology devices can be made with very small-scale dimensions and with sub-circuit structures smaller than the actual bacteria. Such devices are 3-dimensional in nature with a typical biolayer of the acoustic wave biosensor being composed of a cross-link layer and antibody layer overlaid onto the acoustic wave structure. Similarly, nanotechnology devices are also 3-dimensional in nature since beams deflect depending upon the selective attachment of specific substances.

Figure 6:
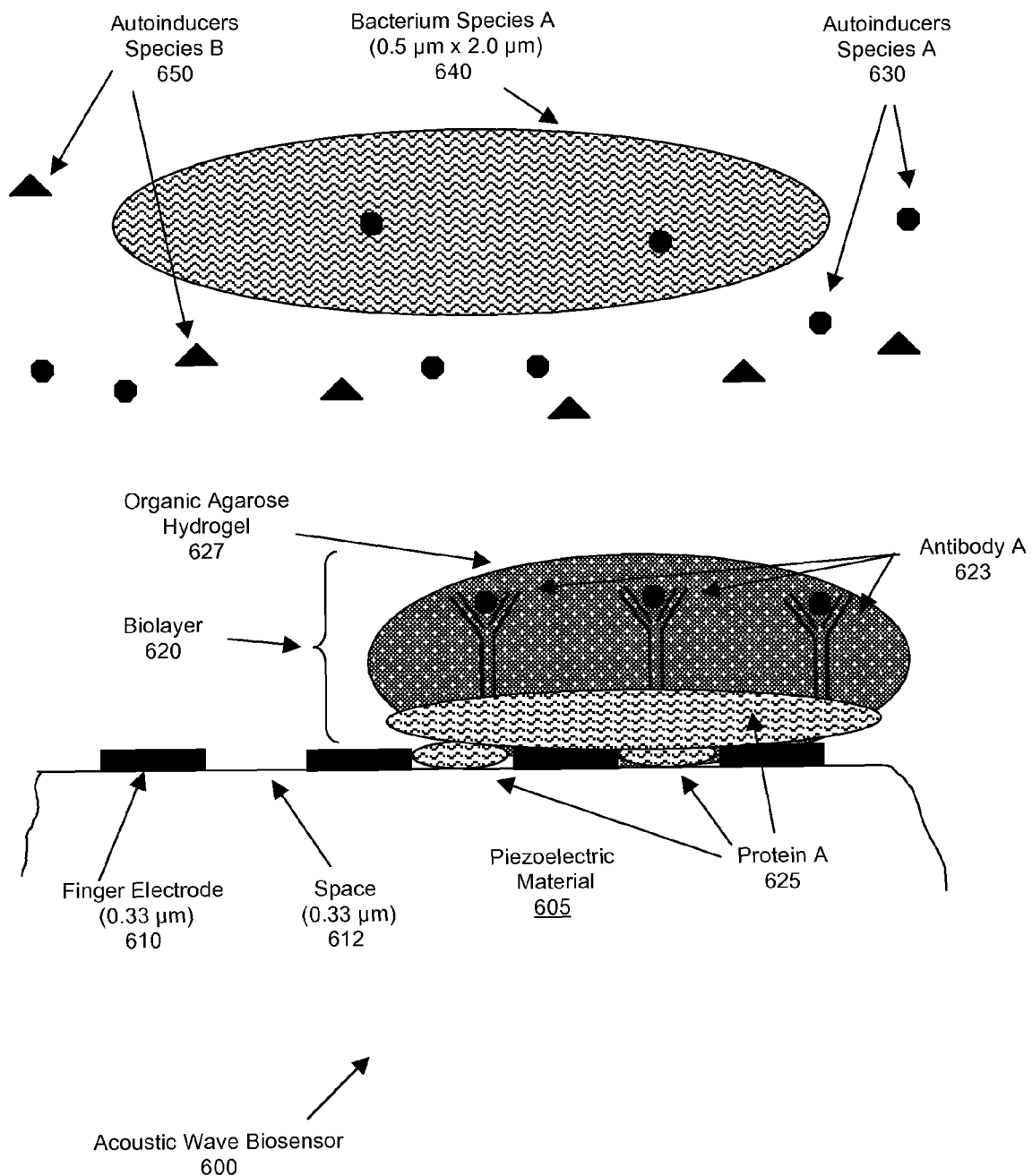
FIG. 6 is a similar view of a SAW device having proteins/antibodies with certain autoinducers binding, a bacterium being placed beside the SAW device to enable dimensions to be compared.

FIG. 6 shows a diagrammatic view illustrating the importance of scale to such detection devices. For this embodiment, an acoustic wave biosensor 600 is constructed on a piezoelectric material 605. The typical width of an interdigital transducer (IDT), finger electrode 610 and space 612 at a frequency of 2.44 GHz is 0.33 μm. Several of the finger electrode widths 610 and adjoining spaces 612 are shown and may constitute a portion of the IDT or a part of a multi-fingered reflector array. A 3-dimensional biolayer 620 is located above certain selected finger electrodes 610 and spaces 612. The biolayer 620 has three main components, namely a bioreceptor molecule, Antibody A 623, a heterobifunctional molecule, Protein A 625 and an organic agarose hydrogel 627. The actual binding of a selected autoinducer with a specific bioreceptor occurs within a rigid thin layer of a specific bioreceptor molecule. Antibody A 623 may be, but is not limited to, an antibody, enzyme, lipid or protein. A thin layer of a specific bioreceptor molecule, Antibody A 623, is attached to the piezoelectric material 605 or the acoustic wave finger electrodes 610 via a heterobifunctional molecule, Protein A 625, such as but not limited to a protein A, alkanethiol. A thin sheath of an organic agarose hydrogel 627 is applied to the device to provide a semi-aqueous environment important for maintaining the three dimensional structure of the receptor molecule.

Above the biolayer 620 are various bacteria autoinducers of species A 630 in vapor form which will bind to an equivalent matched bioreceptor antibody A 623. A bacterium 640 secretes the autoinducer A 630 and is placed above this portion of acoustic wave device 600 to illustrate the scale and difficulty of using this technique to directly detect the bacteria. As the bacteria autoinducers of species A 630 emitted by Bacterium species A 640 bind within the biolayer 620, parameters within the piezoelectric material 605 are altered and therefore change the RF characteristics of the Interdigital Transducer. The IDT finger electrodes 610 are electrically connected to a mechanism to detect this change in RF characteristics. The specificity of the bioreceptor molecule, antibody A 623 is chosen so that the autoinducers of species B 650 are orthogonal or semi-orthogonal with the bioreceptor molecule, antibody A 623.

This example of an acoustic wave biosensor as shown in FIG. 6 illustrates the expediency of detecting signaling molecules such as autoinducers 630 rather than the large Bacterium species 640, such as a *Bacillus Subtilis* spore which measures 1 μm in width at the cross section of the oval shaped organism. The weight of the *Bacillus Subtilis* spore has been estimated to be approximately 1 pico-gram, which would dampen out any acoustic wave when the organism made contact with either the biolayer 620 or the piezoelectric material 605.

The advantages of the present invention will now be readily apparent to a person skilled in the art from the foregoing description of preferred embodiments. Other embodiments of the invention will also now be readily apparent, the scope of the invention being defined in the appended claims.

What is claimed is:

1. An acoustic wave biosensor for detecting and identifying bacteria, micro-organisms or plants in a liquid or gaseous medium, said bacteria, micro-organisms or plants being of the kind which produce autoinducer signaling molecules in intercellular space, said acoustic wave biosensor comprising:
 a plurality of spaced apart electrodes:
  disposed on a substrate of piezoelectric material; and
  having a biolayer matched to a specific type of autoinducer signaling molecule to be detected;
 the biolayer comprising:
  a layer of heterobifunctional molecules comprising protein A disposed on the electrodes and on the piezoelectric material between the electrodes;
  a plurality of bioreceptor molecules which bind exclusively with the specific type of autoinducer signaling molecule to be detected;
  the bioreceptor molecules being supported by the layer of heterobifunctional molecules; and
  a hydrogel layer surrounding the bioreceptor molecules to support a three-dimensional structure thereof;
  so that the bioreceptor molecules can bind with the specific type of autoinducer signaling molecule to be detected;
 whereby the biolayer is reactive to the specific type of autoinducer signaling molecule to be detected such that corresponding autoinducer signaling molecules bind to the biolayer and detectably vary acoustic characteristics of the acoustic wave biosensor.

* * * * *